United States Patent
Sarvetnick et al.

(10) Patent No.: US 6,242,666 B1
(45) Date of Patent: Jun. 5, 2001

(54) ANIMAL MODEL FOR IDENTIFYING A COMMON STEM/PROGENITOR TO LIVER CELLS AND PANCREATIC CELLS

(75) Inventors: Nora Sarvetnick, San Diego; Michelle L. Krakowski, Del Mar; Marcie R. Kritzik, La Jolla, all of CA (US)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 09/212,531

(22) Filed: Dec. 16, 1998

(51) Int. Cl.[7] .................. A01K 67/027; A01K 67/00; A01K 67/033
(52) U.S. Cl. .................. 800/18; 800/13; 800/14
(58) Field of Search .................. 800/8; 536/23.1; 514/44; 435/320.1, 455

(56) References Cited

FOREIGN PATENT DOCUMENTS

| 0 363 125 | 4/1990 | (EP) . |
|---|---|---|
| WO96/11949 | 4/1996 | (WO) . |
| WO96/40872 | 12/1996 | (WO) . |
| WO98/162243 | 4/1998 | (WO) . |
| WO98/26044 | 6/1998 | (WO) . |

OTHER PUBLICATIONS

Peshavaria & Stein, *Pancreatic Growth and Regeneration*, Chapter 4, Sarvetnick, ed. (Karger Lander Systems, 1997).
Jones & Sarvetnick, 29 Horm. Metab. Res. 308–310 (1997).
Krakowski et al., 162 J. Endocrinology 167–175 (1999).
Kritzik et al., 163 J. Endocrinology 523–530 (1999).
Krakowski et al., 154(3) Am. J. Pathology 683–691(Mar. 1999).
Arnush et al., "Growth factors in the regenerating pancreas of gamma–interferon transgenic mice," *Lab Invest* 74: 985–990 (1996).
Gu et al., "Epithelial cell proliferation and islet neogenesis in IFN-g transgenic mice" *Development* 118: 33–46(1993).
Guo et al., "Targeting expression of keratinocyte growth factor to keratinocytes elicits striking changes in epithelial differentiation in transgeic mace," *EMBO J 12*: 973–986 (1993).
Housley et al., "Keratinocyte growth factor induces proliferation of hepatocytes and , epithelial cells throughout the rat gastrointestinal tract." *J Clin Invest 94*: 1764–1777 (1994).
Nguyen, et al., "Expression of keratinocyte growth factor in embryonic liver of transgenic mice causes changes in epithelial growth and differentiation resulting in polycystic kidneys and other organ malformations," *Oncogene 12*: 2109–2119 (1996).
Sarvetnick, et al., "Insulin–dependent diabetes mellitus induced in transgenic mice by ectopic expression of class III MHC and interferon–gamma." *Cell 52*:773–782, (1988).
Yi et al., "Keratinocyte growth factor induces pancreatic ductal epithelial proliferation." *Am J Pathol 145*: 80–85 (1994).
Ebert et al. Molecular Endocrinology 2:227–283, 1988.*
Hammer et al. Journal of Animal Science 63:269–278, 1986.*
Itier et al. Differentiation 60:309–316, Sep. 1996.*
Mullins et al. Journal of Clinical Investigation 97(7):1557–1560, 1996.*
Wall et al. Journal of Dairy Science 80:2213–2224, Sep. 1997.*
Yasuda et al. The Journal of Biological Chemistry 273(51):34413–34421, Dec. 1998.*

* cited by examiner

*Primary Examiner*—Karen M. Hauda
*Assistant Examiner*—Joseph T. Woitach
(74) *Attorney, Agent, or Firm*—Mintz, Levin, Cohn, Ferris, Glovsky and Popeo, P.C.

(57) ABSTRACT

The invention provides animal models, where the ectopic expression of KGF, EGF, or both is under the control of a pancreas-specific promoter, e.g., the insulin promoter. The expression of KGF in the ins-KGF pancreatic islets of Langerhans results in enlarged islets, with substantial proliferation of duct cells within the islet mass, and the presence of albumin and alpha-fetoprotein-producing hepatocytes in the islets of the ins-KGF pancreata. The compositions and methods disclosed are useful for identifying and isolating pancreatic stem/progenitor cells, including a common stem/progenitor to liver cells and pancreatic cells.

3 Claims, No Drawings

ANIMAL MODEL FOR IDENTIFYING A COMMON STEM/PROGENITOR TO LIVER CELLS AND PANCREATIC CELLS

TECHNICAL FIELD

This invention relates to generally to models for identifying and isolating pancreatic stem cells, and in one embodiment, to models for identifying and isolating a common stem/progenitor cell that gives rise to hepatic cells and pancreatic cells.

BACKGROUND OF THE INVENTION

A healthy adult pancreas is usually a developmentally stable organ, but a targeted cell loss or aberrant cell growth and development have pathological consequences. For example, in human Insulin Dependent Diabetes Mellitus (IDDM), autoimmune mechanisms cause the selective and permanent destruction of the insulin-producing beta cells in the islets of Langerhans. The lost cells are not restored in vivo, although Sarvetnick et al. *Cell* 52:773–782 (1988) have shown that beta cells have the potential to regenerate. On the other hand, the proliferation of duct cells can contribute to pancreatic disease pathologies, such as chronic pancreatitis, pancreatic cancer, and cystic fibrosis. Pancreatic duct cell proliferation and differentiation have also been shown by Arnush et al., *Lab Invest* 74: 985–990 (1995) to play a critical role in a transgenic mouse model of islet regeneration. Further, endocrine cell differentiation is frequently seen in pancreatic duct cell carcinomas, suggesting that duct cell proliferation can lead to islet neogenesis.

Growth factors are critical for modulating cellular proliferation and differentiation. The growth factors that regulate and promote pancreatic growth are not well characterized, but keratinocyte growth factor (KGF), a member of the fibroblast growth factor family, is known to be involved in wound healing and in the differentiation of many epithelial tissues. KGF upregulates epithelial cell proliferation and pancreatic duct cell proliferation in rats. Also, epidermal growth factor (EGF) and transforming growth factor beta-1 (TGFβ-1) can induce ductal and endocrine cell development, respectively. EGF, which is known to stimulate epithelial cell and fibroblast proliferation, also has mitogenic properties for pancreatic growth. The overexpression of EGF and EGF receptor (EGF-R) is linked both to chronic pancreatitis and to malignant pancreatic growth.

Yi et al. (*Am J Pathol* 145: 80–85, 1994) have shown that systemic administration of KGF to rats induces pancreatic duct cell proliferation. KGF stimulated the proliferation of pancreatic ductal epithelial cells in rats after daily systemic injection for 1–2 weeks. Duct cell proliferation was predominantly adjacent to or within the islets of Langerhans and occurred in the absence of physical injury to the pancreas. However, knockout mice lacking KGF do not display significant developmental abnormalities, and pancreatic and liver development appear entirely normal (Guo et al., *EMBO J* 12: 973–986, 1993).

Clearly, KGF can in some way influence pancreatic growth, and further studies designed to investigate its role in this process would be of considerable value. It is therefore important to expand our knowledge of these growth factors by providing animal models allowing the study of liver and pancreatic growth and development, and associated disease states.

SUMMARY OF THE INVENTION

The invention provides animal model systems for identifying pancreatic stem/progenitor cells, and in one embodiment, a common stem/progenitor cell which gives rise to liver cells (hepatocytes) and pancreatic cells. The animal model ectopically expresses KGF from a pancreatic specific promoter, for example, the insulin promoter (ins-KGF). Transgenic animals that express KGF in pancreatic islets of Langerhans have enlarged islets, with substantial proliferation of duct cells within the islet mass. The animals also have albumin and alpha-fetoprotein-producing hepatocytes in the islets. The transgenic animals show no pathology, hyperglycemia, or hypoglycemia associated with the KGF expression.

The invention further provides transgenic EGF and EGF× KGF animals, in both of which the ectopic expression of the growth factors is under the control of a pancreatic specific promoter. Animals with beta cell-targeted expression of EGF show significant morphological changes, including cellular proliferation and disorganized islet of Langerhans growth. EGF×KGF transgenic animals experience more profound changes in pancreatic morphology than do single transgenic animals. Double transgenic animals also show proliferation of pancreatic cells and extensive intra-islet fibrosis, which increases in severity with time. The animals of the invention are useful for the study of the effects of EGF and KGF on pancreatic growth and development, and for the study of pathologies associated with aberrant overexpression of EGF or KGF.

The invention provides several distinct cell types, including pancreatic hepatocytes, derived from a common stem/progenitor to liver cells and pancreatic cells. The invention also provides transgenic duct cells, and transgenic amylase-producing cells. The invention further provides methods of making and proliferating the transgenic cells and methods of using the transgenic cells.

The invention provides for the proliferation and differentiation of common stem/progenitor cells in vivo. A common stem/progenitor to liver cells and pancreatic cells is contacted in vivo with a developmentally effective amount of a growth factor. The growth factor induces the growth factor-responsive cells to differentiate. When the genetic modification is for the production of a biologically active substance, the substance will generally be one that is useful for the treatment of a given disorder. The invention thus provides methods for inducing specific cell types, including hepatocytes, duct cells, and amylase-producing cells. An interesting aspect of these methods of the invention is the underlying scientific information regarding the development of the specific cells in the pancreas. This useful scientific information results from the generation of the animal models of the invention.

The invention provides a method for the transfection of a common stem/progenitor to liver cells and pancreatic cells with vectors which can express the gene products for growth factors or growth factor receptors.

The invention provides a pancreactic duct culture. The pancreatic duct culture is useful for the development of a stem cell assay for identifying a common stem/progenitor cell in pancreatic islets.

The invention provides a method for using the homeobox protein PDX-1 as a marker for identifying a common stem/progenitor to liver cells and pancreatic cells. Antibodies to PDX-1 are used to revealed the presence of PDX-1 nuclear staining in a subset of ductal cells bordering the lumen, as well as in a subset of perilumenal ductal cells. No differences are observed in morphology between those ductal cells which expressed PDX-1 and those which did not, but insulin expression, characteristic of the newly formed islet structure, is present in a subpopulation of PDX-1 expressing ductal cells.

DETAILED DESCRIPTION

Introduction The invention provides animals, where the expression of EGF, KGF, or both EGF and KGF is under the control of a pancreatic specific promoter, e.g., the insulin promoter. As such, the invention provides an animal model system for identifying and isolating pancreatic stem/progenitor cells and for identifying and isolating a cell which is a common stem/progenitor for liver cells (hepatocytes) and pancreatic cells.

A definition of a "stem cell" is provided by Potten & Loeffler, *Development,* 110:1001 (1990), who have defined stem cells as "undifferentiated cells capable of (a) proliferation, b) self-maintenance, (c) the production of a large number of differentiated functional progeny, (d) regenerating the tissue after injury, and (e) a flexibility in the use of these options." Stem cells are used in a body to replace cells that are lost by natural cell death, injury or disease. The presence of stem cells in a particular type of tissue usually correlates with tissues that have a high turnover of cells, stem cells are also present in tissues, e.g., liver (Travis, *Science,* 259:1829, 1993), that do not have a high turnover of cells. A "progenitor" cell is typically defined as having the capability to divide for several generations, but not self renew. Progenitor cells also typically are defined to be capable of differentiating into a variety of different cell types.

As used herein, a common stem/progenitor to liver cells and pancreatic cells is an undifferentiated cell that can be induced to proliferate using the methods of the present invention, and that can upon differentiation, form pancreatic cells, including, e.g., pancreatic duct cells, as well as liver cells, including, e.g., hepatocytes. Such cells are "multipotent" because the progeny have multiple differentiation pathways. The animal models of the invention is useful for identifying both common stem cells and progenitor cells.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

Molecular biological methods for making the animal models of the invention The invention provides transgenic cells and transgenic animals in which the expression of an EGF-coding polynucleotide, a KGF-coding polynucleotide, or both an EGF-coding polynucleotide and a KGF-coding polynucleotide is under control of a pancreatic-specific promoter. The animal can be any non-human animal, preferably rodent, and most preferably mouse.

The term "transgenic" is used to describe a cell that contains exogenous genetic material or an animal that contains exogenous genetic material within most of the animal's cells. A transgene is a piece of DNA that is inserted by artifice into a cell, and becomes part of the genome of the organism (either stably integrated or as a stable extrachromosomal element) that develops from that cell. The term "transgenic" also describes any transgenic technology known to those in the art that can produce a cell or animal carrying an introduced transgene. Included within this definition is a transgene created by the providing of an RNA that is transcribed into DNA and then incorporated into the genome.

The transgenes of the invention include DNA polynucleotides that encode EGF and KGF, operably linked to an insulin promoter for expression in insulin-producing cells (i.e., the beta cells of the pancreas). "Operably linked" refers to a juxtaposition where the polynucleotide components are configured so as to perform their usual function. Thus, a promoter operably linked to a coding polynucleotide is can effect the expression of the coding polynucleotide. A "promoter" is a sequence sufficient to direct transcription. An "operably linked" coding polynucleotide and promoter are connected in such a way as to permit gene expression when the appropriate molecules (e.g., transcriptional activator proteins) are bound to the regulatory sequence. Included in the invention are those promoter elements which are sufficient to render promoter-dependent gene expression inducible.

Pancreatic-specific promoters are promoters that preferentially act in the pancreas to express the coding polynucleotides to which they are operably linked. Among the pancreatic promoters are the insulin promoter, the glucagon promoter, the glucagon receptor promoter, and the GLP-1 receptor promoter. The insulin promoter is used in EXAMPLES 1, 2, 3, and 4.

Glucagon is a 29 amino acid hormone produced in human A-cells of the pancreas. Glucagon promote glycogenolysis and gluconeogenesis, which causes an increase in the level of blood sugar, by binding to specific cell-surface receptors found on insulin producing cells, which in turn causes the level of insulin to rise. As the level of insulin rises, insulin down regulates the production of glucagon, completing the feedback loop. Glucagon is translated from a 630 base pair gene to form the precursor preproglucagon, which is subsequently post-translationally truncated to proglucagon. Proglucagon is subsequently cleaved into three discrete highly homologous individual peptides called glucagon, glucagon-like protein 1, and glucagon-like protein 2. GLP-1 and GLP-2 are 37 and 34 amino acids respectively and are found in the pancreas. GLP-1 is perhaps the most potent insulinotropic hormone to be characterized and is widely considered as a potential successful new agent for the treatment of type II diabetes, because its activity is preserved in patients with this disease. Several studies have evaluated the therapeutic potential of GLP-1 in the control of diabetic hyperglycemia in human patients (see for example, Gutniak et al., *N. Engl. J. Med.* 326, 1316–22 (1992)).

A "transgenic animal" is an animal whose genome has been altered by human intervention. The "transgenic animals" of the invention are produced by introducing "transgenes" into the germline of the animal. A transgenic animal can further be produced by cross-breeding two chimeric animals which include exogenous genetic material within cells used in reproduction. 25% of the resulting offspring will be transgenic i.e., animals which include the exogenous genetic material within all of their cells in both alleles; 50% of the resulting animals will include the exogenous genetic material within one allele; and 25% will include no exogenous genetic material.

Embryonal target cells at various developmental stages can be used in which to introduce transgenes. Different methods are used depending on the stage of development of the embryonal target cell. The zygote is the best target for micro-injection. The use of zygotes as a target for gene transfer has a major advantage in that the injected DNA can be incorporated into the host gene before the first cleavage. Most or all the cells of the transgenic non-human animal carry the incorporated transgene. This is also reflected in the efficient transmission of the transgene to offspring of the founder, as 50% of the germ cells will harbor the transgene.

Retroviral infection can also be used to introduce transgene into an animal. The developing embryo can be cultured in vitro to the blastocyst stage, during which time the blastomeres can be targets for retro viral infection. Efficient infection of the blastomeres is obtained by enzymatic treatment to remove the *zona pellucida*. The viral vector system used to introduce the transgene is typically a replication-defective retrovirus carrying the transgene. Transfection is easily and efficiently obtained by culturing the blastomeres on a monolayer of virus-producing cells. Infection can alternatively be performed at a later stage. Virus or virus-producing cells can be injected into the blastocoel. Most of the founders are mosaic for the transgene, because incorporation occurs only in a subset of the cells which formed the transgenic animal. Further, the founder can contain various retroviral insertions of the transgene at different positions in the genome which generally will segregate in the offspring. It is also possible to introduce transgenes into the germ line, albeit with low efficiency, by intrauterine retroviral infection of the midgestation embryo.

A third type of target cell for transgene introduction is the embryonal stem cell (ES). ES cells are obtained from pre-implantation embryos cultured in vitro and fused with embryos. Transgenes can be efficiently introduced into the ES cells by DNA transfection or by retrovirus-mediated transduction. Transformed ES cells can thereafter be combined with blastocysts from an animal. The ES cells thereafter colonize the embryo and contribute to the germ line of the resulting chimeric animal (for a review, see Jacnisch, *Science* 240: 1468–1474, 1988).

Recombinant genetic techniques well known in the art can be used for practicing the methods of the inventions, including measuring DNA content, Southern blotting, Northern blotting, PCR analysis, and uptake of radioactive or fluorescent nucleotides. As used in this patent, the term "recombinant" always refers to a product of human intervention. Literature sources for molecular biological techniques include Berger & Kimmel (*Guide to Molecular Coning Techniques, Methods in Enzyinology,* Vol. 152, Academic Press, Inc., San Diego, Calif.); Sambrook et al. (*Molecular Cloning—A Laboratory Manual,* 2d Edition, Vol. 1–3, Cold Spring Harbor Laboratory, Cold Spring Harbor Press, New York, 1989); and *Current Protocols in Molecular Biology* (Ausubel et al., Eds., Current Protocols, 1994 Supplement). Useful information is also found in product information from manufacturers of biological regents and experimental equipment, such as the SIGMA Chemical Company (St. Louis, Miss.), R&D Systems (Minneapolis, Minn.), Pharmacia LKB Biotechnology (Piscataway, N.J.), CLONTECH Laboratories, Inc. (Pal Alto, Calif.), Chem Genes Corp., Aldrich Chemical Company(Milwaukee, Wis.), Fluka Chemica Biochemika Analytika (Fluka Chemie AG, Buchs, Switzerland), and Applied Biosystems (Foster City, Calif.). Methods for the polymerase chain reaction (PCR), the ligase chain reaction (LCR), Qβ-replicase amplification and other RNA polymerase mediated techniques (e.g., NASBA) are also Mullis et al. (U.S. Pat. No. 4,683,202); *PCR Protocols A Guide to Methods and Applications* (Innis et al., Eds., Academic Press Inc., San Diego, Calif., 1990), Arnheim et al., (*C&EN,* 36–47, Oct. 1, 1990); *The Journal Of NIH Research* (3: 81–94, 1991); Kwoh et al. (*Proc. Natl. Acad. Sci. USA,* 86: 1173, 1989); Guatelli et al. (*Proc. Natl. Acad. Sci. USA,* 87: 1874, 1990); Lomell et al. (*J. Clin. Chem,* 35: 1826, 1989); Landegren et al. (*Science 241: 1077–1080, 1988*); Van Brunt (*Biotechnology 8: 291–294, 1990*); Wu & Wallace (Gene 4: 560, 1989); Barringer et al. (*Gene* 89: 117, 1990); and Sooknanan & Malek (*Biotechnology* 13: 563–564, 1995).

Ins-KGF animal The invention provides transgenic animals and cells in which expression of a KGF-coding polynucleotide is under control of is under control of a pancreatic-specific promoter, such as an insulin promoter. The ins-KGF animal directs KGF expression to the insulin-producing cells (e.g., the beta cells) of the islets of Langerhans in the pancreas.

Keratinocyte growth factor (KGF) is a mesenchymally-derived mitogen that acts as a potent mitogen specific for epithelial cells. In vivo, KGF can also induce mesenchymal stimulation of epithelial cell proliferation. Further, KGF is important in the wound healing process and epithelial cell differentiation.

KGF is a member of the fibroblast growth factor family. Members of this family influence a number of processes, including cell proliferation, migration, and differentiation. KGF is a protein of 22.5 kDa with a length of 194 amino acids inferred from the cDNA sequence. Human KGF is a 19 kilodalton (kDa) protein containing 163 amino acid residues. KGF genes are present in the genomes of animals at least as diverse as chimpanzee, gorilla, gibbon, African green monkey, macaques, mice, and chickens. KGF is called also HBGF-7 (heparin-binding growth factor-7) and the recommended new name is FGF-7 (fibroblast growth factor-7). The bovine counterpart of KGF is SDGF-3 (spleen-derived growth factor). The KGF receptor has recently been cloned. The KGF receptor encodes a tyrosine and is a member of the family of receptors binding aFGF and bFGF.

Beta cells are insulin-producing cells located in the pancreatic islets of Langerhans. The pancreas is located in the abdomen, behind the stomach. Inside the pancreas are small clusters of cells called Islets of Langerhans. Within the islets are beta cells, which produce insulin. Insulin is a hormone that regulates the amount of sugar in the blood. In the beta cells, insulin expression results from expression of an insulin-coding polynucleotide under the control of an insulin promoter.

The prior art has shown that transgenic expression of KGF in the liver during development results in substantial morphological changes to the liver, the pancreas, and other sites, as well as changes in epithelial growth in multiple organ systems (Nguyen et al., *Oncogene* 12: 2109–2119, 1996). This is in contrast to the ins-KGF animal of the invention, where transgenic expression of KGF is directed to the pancreas and where significant morphological disturbances are not exhibited outside of the pancreas.

The ins-KGF animals of the invention are healthy, with no obvious toxic effects due to pancreatic KGF expression. For example, no significant differences is found in the blood glucose levels of ins-KGF mice compared to age-matched littermate control mice is detected (see, EXAMPLE 1). Indeed, there is no evidence to suggest that there is any change in pancreatic activity which is significant or which causes pathology.

Several interesting features characterize the ins-KGF animal of the invention, including the development of hepatocytes in the islets of Langerhans. The islets of Langerhans are clusters of alpha, beta, delta, and polypeptide cells located throughout the pancreas. The ins-KGF hepatocytes are located at the periphery of the islets and are identified by expression of albumin and alpha-fetoprotein. Both the liver and pancreas are derived from a common endodermal evagination from the foregut. In this regard, it is significant that these ins-KGF hepatocytes produce alpha-fetoprotein, an embryo-specific protein not normally found in the adult pancreas except in those cases where hepatocytes are just developing. All the ins-KGF hepatocytes express alpha-fetoprotein, whereas only ⅔ express albumin. Alpha-fetoprotein is expressed at earlier times during development than is albumin, so the cells expressing alpha-fetoprotein but not albumin represent an earlier hepatocyte precursor than do the double positive cells. Still, hepatocyte localization within the islet structure is an anomaly and indicates the presence of a common stem/progenitor to liver cells and pancreatic cells in the developing pancreas.

The induction of hepatocytes by KGF in the ins-KGF animal of the invention was not expected. KGF has been shown to induce the proliferation of hepatocytes in vitro and in vivo (Housley et al., *J Clin Invest* 94: 1764–1777, 1994; Itoh et al., *Biochem. Biophys. Res. Commu.* 192: 1011–1015, 1993). Hepatocytes are also induced in the pancreas of transgenic mice overexpressing IFNy in the islets of Langerhans (Amush et al., *Lab Invest* 74: 985–990, 1995). By contrast to these models, most of the hepatocytes in the ins-KGF animal of the invention are located within the pancreas at the outer edges of the islets.

Another interesting features characteristic of the ins-KGF animal of the invention is the hyperproliferation of duct cells in the pancreas of transgenic animals. In the normal pancreas, intercalated ducts are present and extend into the acinar lumen. The ducts of the exocrine pancreas include (1) the intercalated ducts formed by low cuboidal epithelium; (2) the intralobular ducts, which vary in diameter and are lined by simple cuboidal epithelium; and (3) interlobular ducts that are larger, lined by simple columnar epithelium, and invested by a layer of collagenous tissue. Two major ducts are the ducts of Santorini and Wirsung; they have tall columnar epithelium with basal nuclei.

In the normal (nontransgenic) pancreas, cells that produce digestive enzymes are clumped into groups, called acini, that lead into ducts through which enzymes are delivered to the duodenum. Cells within the ducts are duct cells. Cells within an acinus, the acinar cells, constitute the majority of the pancreas. The apical portion of an acinar cell is filled with eosinophilic zymogen granules. The acinar cells secrete directly into acinar lumen through the apical surface. Secretion of proenzymes by the acinar cells is regulated by secretin, cholecystokinin, and nerve stimulation from the vagus.

The proliferating duct cells are identified as duct cells by expression of carbonic anhydrase II (CAII). The proliferating duct cells are located within the islets of Langerhans, which exhibit normal production of all endocrine hormones.

By contrast to previous work by Yi et al. (*Am J Pathol* 145: 80–85, 1994), the pancreas of the ins-KGF animal model of the invention continually expresses KGF without the need for continual or additional treatment. The duct cell proliferation is an ongoing process during the life of the ins-KGF animal of the invention, without pathological consequences. Interestingly, the influence of KGF on duct cell proliferation in the ins-KGF animal of the invention parallels much of what is observed after systemic administration of KGF in rats. Indeed, it is striking that the intralobular ducts adjacent to or within the islets of Langerhans are those that proliferate.

Ins-EGF animals The invention provides transgenic animals and cells in which the expression of EGF is targeted to the pancreas. In one embodiment, expression of EGF is targeted to beta cells in the islets of Langerhans. Epidermal growth factor (EGF) is a potent mitogen for a variety of cells of endodermal, mesodermal and ectodermal origin. EGF also promotes the growth and migration of keratinocytes and enhances the proliferation of fibroblasts and embryonic cells. Thus, EGF plays an important role in wound healing and organogenesis.

EGF is a globular protein of 6.4 kDa consisting of 53 amino acids. It contains three intramolecular disulfide bonds essential for biological activity. EGF proteins are evolutionary closely conserved. Human EGF and murine EGF have 37 amino acids in common. Murine EGF is purified from male mouse submaxillary glands as a 6.1 kDa protein. Human recombinant EGF can be produced in *E. coli* as a 6 kDa protein containing 53 amino acid residues. Human and murine EGF are species cross-reactive. Approximately 70% homology is found between human EGF and EGF isolated from other species. The relative positions of the cysteine residues is conserved.

EGF is known to induce duct cell development. While the ability of EGF to stimulate epithelial cell and fibroblast proliferation is well documented, EGF also has mitogenic properties for pancreatic growth. In addition, evidence exists linking the overexpression of EGF and its receptor (EGF receptor, EGF-R) to both chronic pancreatitis and malignant pancreatic growth. For example, the remarkable proliferative and differentiation patterns of the ins-IFNγ mouse, EGF and EGF-R were found to be upregulated by Arnush et al., *Lab Invest* 74: 985–990 (1995). The EGF receptor is a 170 kDa monomeric glycoprotein with intrinsic tyrosine kinase activity. Stimulation of the receptor kinase activity occurs when EGF binds to the extracellular domain of the receptor resulting in autophosphorylation of the receptor's cytoplasmic tail and transduction of the EGF proliferative signal.

Ins-EGF animals have dramatic morphological changes in the pancreata as compared with non-transgenic animals. Pancreatic cell proliferation occurs in the ins-EGF animals. The ins-EGF animals also exhibit disorganized islets and intra-islet fibrosis.

Ins-EGF×KGF animals The invention provides transgenic animals in which the expression of KGF and EGF is targeted to the pancreas. In one embodiment, the expression of KGF and EGF is targeted to the beta cells in the islets of Langerhans. Both KGF and EGF play important roles in pancreatic development. Although a low basal level of EGF is normally expressed in the islets of non-transgenic mice, KGF is not normally found in the islets of Langerhans. While the ins-EGF×KGF animals are useful for addressing the cooperative effects that localized overproduction of EGF and KGF has on pancreatic growth and function, the ins-EGF and ins-KGF transgenic mice are useful for assessing the influences independently.

The ins-EGF×KGF animals of the invention show that expression of EGF and KGF in islet beta cells generates an accelerated and extensive series of changes to both endocrine and exocrine tissues. For example, significant intra-islet duct cell proliferation occurs in the pancreata of ins-KGF animals. Also, hepatocytes occur within the islets of ins-EGF×KGF animals. The ins-EGF×KGF animals have disorganized islets and intra-islet fibrosis, both of which are more extensive in the ins-EGF×KGF animals than in the ins-EGF×KGF animals. Many features shared by both single transgenic animals, such as pancreatic cell proliferation, increased size and disorganization of islets, and fibrosis, occur to a greater extent in the double transgenic animals. Interestingly, amylase-positive cells in the double transgenic animals are not found in either of the single transgenic animals, indicating that localized overexpression of both EGF and KGF in beta cells is required to produce this unique phenotype.

Despite the extensive morphological changes in the pancreata of growth factor transgenic animals, no deficiencies in pancreatic function are detected. Normal endocrine hormones and exocrine enzymes are present in these transgenic animals. Blood glucose levels remain normal throughout the lives of the animals. Thus the physical changes apparent in these animals do not interfere with normal pancreatic function.

Interestingly, some of the morphologies observed also characterize several pancreatic diseases. For example, the GK rat model of Non-Insulin-Dependent Diabetes Mellitus (NIDDM) is characterized by disorganized islets, significant fibrosis, and clusters of beta cells separated by strands of connective tissue (Movassat et al, *Diabete Metab* 21: 365–370, 1995). Chronic pancreatitis is characterized by inflammation and fibrosis. Interestingly, in chronic pancreatitis and in some human pancreatic cancers, EGF, EGF-R, and KGF are often overexpressed.

In vivo proliferation and differentiation of common stem cell/progenitor to specific liver and pancreatic cell types The invention provides methods for inducing specific cell types, including hepatocytes, duct cells, and amylase-producing cells. A common stem/progenitor to liver cells and pancreatic cells is contacted in vivo with a developmentally effective amount of a growth factor, wherein growth factor induces the growth factor -responsive cells to develop to hepatocytes, proliferating duct cells, or amylase producing cells, among others. A "developmentally effective amount," in reference to the growth factor-dependent development of a cell type, refers to an amount of growth factor sufficient to bring about the development of the cell type. A developmentally effective amount can be determined by those of skill in the art using known cell culture techniques.

The growth factors include any growth factor known in the art. Pharmaceutical compositions include any substance that blocks the inhibitory influence or stimulates common stem/progenitor cells to proliferate and ultimately differentiate. Thus, techniques to proliferate, differentiate, and genetically modify common stem/progenitor cells in vitro can be adapted to in vivo techniques, to achieve similar results. Such in vivo manipulation and modification of these cells allows cells in an animal, that are lost due to injury or disease, to be endogenously replaced, thus obviating the need for transplanting foreign cells into a patient. Additionally, the cells of the invention can be modified or genetically engineered in vivo so that they express various biological agents useful in the treatment of neurological disorders.

Administration of growth factors to a subject can be done by any method, including injection cannula, transfection of cells with growth hormone-expressing vectors (such as ins-EGF cells, ins-KGF cells, and ins-EGF×KGF cells), injection, timed-release apparati which can administer substances at the desired site, and the like. Pharmaceutical compositions can be administered by any method, including injection cannula, injection, oral administration, timed-release apparati and the like. The common stem/progenitor cells proliferate and differentiate in vivo after induction with particular growth factors or pharmaceutical compositions which will induce their proliferation and differentiation. Therefore, this latter method circumvents the problems associated with transplantation and immune reactions to foreign cells. Any growth factor can be used, particularly EGF and KGF.

The normal fate of the in vivo cell population of common stem/progenitor cells (i.e. cell death) can be altered by administering Bcl-2 or genetically modifying the cells with the bcl-2 gene. Bcl-2 and related gene products are known to prevent programmed cell death (apoptosis) in a variety of cell types. Similar to the EGF administration, a clonal expansion of common stem/progenitors to liver cells and pancreatic cells can be achieved following infection with bcl-2.

The invention thus provides an animal model system to characterize the in vivo mechanisms that regulate hepatocyte proliferation and differentiated function during liver regeneration. It is known that liver injury causes the release of multiple factors which regulate cellular proliferative activity. These factors are produced both by the liver and by other tissues and, in other situations, their trophic actions are not limited to liver cells. However, cellular mechanisms restrict subsequent cellular proliferation to the injured liver, so that cellular proliferation does not increase in other injured organs. Each of these different growth-regulatory factors interact with unique receptors on the surface of hepatocytes and trigger a complex, yet orderly, cascade of events within the cell that, together, culminate in a "re-programming" of the hepatocyte's gene expression which, in turn, permits the cell to escape growth arrest. Basic investigation of cellular proliferation is often performed with isolated cells in simplified culture systems. However, this strategy ignores other important influences (e.g., cell-cell and cell-environment interactions) that regulate cellular proliferation and differentiation in living animals. The latter are better studied in models which leave organ architecture intact. In addition, the latter models are necessary to identify responses of other liver components (including bile duct cells, blood vessels, the connective tissue) which are also involved in reconstitution of the liver after injury.

In vivo genetic modification of a common stem/progenitor to liver cells and pancreatic cells Any appropriate method of genetic modification can be used for the genetic modification of common stem/progenitor to liver cells and pancreatic cells. The term "genetic modification" means the stable or transient alteration of the genotype of a cell by intentional introduction of exogenous DNA. DNA may be synthetic, or naturally derived, and may contain genes, portions of genes, or other useful DNA sequences. The term "genetic modification" does not include naturally occurring alterations such occur through natural viral activity, natural genetic recombination, or the like. When the genetic modification is for the production of a biologically active substance, the substance will generally be one that is useful for the treatment of a given disorder, for example, to secrete a certain growth factor product. The term "growth factor product" means a protein, peptide, mitogen, or other molecule having a growth, proliferative, differentiative, or trophic effect.

A common stem/progenitor to liver cells and pancreatic cells can be modified in vivo. The genetic modification can be accomplished using an expression vector. Any expression vector known in the art can be used to express the growth factor, as long as it has a promoter which is active in the cell, and appropriate termination and polyadenylation signals.

For a mammalian subject host, several possible vector systems are available for expression of the polynucleotide specific for a targeted transcript. Some vectors use DNA elements which provide autonomously replicating extra-chromosomal plasmids, generally derived from animal viruses. Other vectors include vaccinia virus expression vectors. Still other vectors integrate the desired polynucleotide into the host chromosome. Cells which have stably integrated the introduced DNA into their chromosomes can be selected by also introducing one or more markers (e.g., an exogenous gene) which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription termination signals.

A number of strategies have been employed to mark donor cells, including tritiated labels, fluorescent dyes, dextrans, and viral vectors carrying reporter genes. However, these methods suffer from inherent problems of toxicity, stability, or dilution over the long term. The use of cells derived from transgenic animals may provide an improved means by which identification of transplanted neural cells can be achieved. A transgenic marking system provides a more stable and efficient method for cell labeling. In this system, promoter elements can direct the expression of the *E. coli* β-galactosidase reporter gene in transgenic mice. In these systems, cell-specific expression of the reporter gene occurs in a developmentally-regulated manner. The Rosa26 transgenic mice is one example of a transgenic marking system in which all cells ubiquitously express β-galactosidase. Embryonic or adult Rosa 26 mice are transgenic animals derived from C57/BL/6 mice, which express the β-galactosidase gene in all cells, thus allowing the transplanted cells to be easily detected in host tissue.

Virus-like vectors are useful as vehicles for the importation and expression of recombinant polynucleotide constructs in cells. Virus-derived vectors can safely deliver exogenous nucleic acid to a recipient cell. Virus-derived vectors that carry a heterologous gene (transgene) to exploit the natural ability of a virus to deliver genomic content to a target cell are useful for gene therapy to correct genetic disease or to deliver therapeutic molecules and generally will contain viral, for example retroviral long terminal repeat (LTR), simian virus 40 (SV40), cytomegalovirus (CMV); or liver (such as the albumin promoter; see, Connelly et al., *Hum Gene Ther.* 6(2):185–93 (1995) and Milos & Zaret, *Genes Dev.* 6(6):991–1004 (1992)) or pancreatic cell-specific promoters (such as insulin promoters).

To produce recombinant viral vectors for mammalian cells, several viruses have been developed. These include recombinant vaccinia virus vectors and vectors derived from various smaller viruses. Interest has centered on four types; retroviruses (including lentiviruses), adenoviruses, adeno-associated viruses and herpes simplex virus type I (see, David Peel, *Virus Vectors & Gene Therapy: Problems, Promises & Prospects* (MBChB Special Study Module Project Report, Department of Microbiology & Immunology, University of Leicester,1998)).

Generally, such vectors do not replicate in vivo, precluding any unintended infection of non-target cells. In such cases, helper cell lines are provided which supply the missing replicative functions in vitro, thereby permitting amplification and packaging of the vector encoding the polynucleotide. A further precaution against accidental infection of non-target cells involves the use of target cell-specific regulatory sequences. When under the control of such sequences, polynucleotide constructs would not be expressed in normal tissues (see, U.S. Pat. No. 5,824,544, issued Oct. 20, 1998 to Armentano et al., which provides adenovirus vectors for use in gene therapy that prevent the generation of replication-competent adenovirus during in vitro propagation and clinical use).

Retroviruses are a class of enveloped viruses containing a single stranded RNA molecule as the genome. Retroviral vectors are frequently used for or gene therapy, because of their ability to integrate into the cellular genome (Jolly, *Cancer Gene Therapy* 1: 51–64 (1994); Hodgson, *Bio Technology* 13: 222–225 (1995)).Retroviral vectors can be based upon the Moloney murine leukemia virus (Mo-MLV). Mo-MLV is an amphotrophic virus, capable of infecting both mouse cells and human cells. This capability enables vector development in both mouse models and human cells, thus enabling human treatment. The viral genes are replaced with the transgene of interest and expressed on plasmids in the packaging cell line.

Adenoviruses are non-enveloped viruses containing a linear double stranded DNA genome, which has been well-characterized through studies in classical genetics and molecular biology (Horwitz, in *Virology*, 2nd ed., Fields et al., eds. (Raven Press, New York, 1990). Subgroup C serotypes 2 or 5 are usually used as vectors. The life cycle does not normally involve integration into the host genome, rather adenoviruses replicate as episomal elements in the nucleus of the host cell. Adenovirus-based vectors offer several unique advantages, including tropism for both dividing and non-dividing cells, minimal pathogenic potential, ability to replicate to high titer for preparation of vector stocks, and the potential to carry large inserts (Berkner, *Curr. Top. Micro. Immunol.* 158: 39–66 (1992); Jolly, *Cancer Gene Therapy* 1: 51–64 (1994). Adenoviral vectors are very efficient at transfecting cells in vitro and in vivo, and can be produced at high titers. Transgene expression in vivo from early-developed vectors tended to be transient. The development of vectors containing fewer genes, culminating in the "gutless" vectors which contain no viral coding sequences, has resulted in prolonged in vivo transgene expression in liver tissue (Schieder et al., *Nature Genetics* 18: 180–183 (1998)).

Adeno-associated viruses (AAV) are non-pathogenic human parvoviruses, dependent on a helper virus to proliferate. AAV are capable of infecting both dividing and non dividing cells, and in the absence of a helper virus integrate into a specific point of the host genome (chromosome 19q 13-qter) at a high frequency. Recombinant AAV can also efficiently integrate into the host genome, can transduce non-dividing cells, and does not induce an immune response which destroys the transfected cells. Interest in AAV vectors has been due to AAV integration into the host genome allowing prolonged transgene expression. Gene transfer into hepatic cells has been reported by Snyder et al., *Nature Genetics* 16: 270–275 (1997).

When a retroviral construct is to be used to genetically modify common stem/progenitor cells, these cells can be proliferated, for example, using an osmotic infusion pump to deliver growth factors to the pancreas several days prior to infection with the retrovirus.

The genetic modification of common stern/progenitor cells can be performed by transfection using methods known in the art including CaPO$_4$ transfection, DEAE-dextran transfection, by protoplast fusion, electroporation, lipofection, and the like. With direct DNA transfection, cells can be modified by particle bombardment, receptor mediated delivery, and cationic liposomes.

Non-viral polynucleotide constructs are also useful as vehicles for the importation and expression of polypeptide of interest in cells. polynucleotide constructs can be directly injected into tissue. Methods of direct injection of polynucleotides into tissue arc described by Blau & Springer, *N Engl J Med* 333(23):1554–6 (1995). See also, Blau & Khavari, *Nat Med* 3(6): 612–3 (1997) The polynucleotide constructs can be chemically encapsulated for transfection, as described by Wu el al., *J Biol Chem* 264(29): 16985–7 (1989). Wu et al. showed that a foreign gene driven by natural mammalian regulatory elements can be targeted to hepatocytes and the resultant gene expression made to persist. A soluble DNA carrier system was constructed of two covalently linked components: (1) a polycation, poly-L-lysine, that can bind DNA in a strong but non-damaging interaction, and (2) an asialoglycoprotein which can be targeted specifically to hepatocytes by cell surface asialoglycoprotein receptors unique to this cell type. Wu et al. used a plasmid containing mouse albumin regulatory sequences (making this system attractive for use with the methods of the invention) and complexed to the carrier system for intravenous injection. By this system, the polynucleotide constructs can be delivered to hepatocytes by intravenous injection in vivo using a soluble DNA carrier system. Gene expression targeted in this manner can be made to persist by stimulation of hepatocyte replication.

The polynucleotide constructs can also be introduced into cells by the method of Kaneda et al., *Science* 243(4889): 375–8 (1989) By this method, polynucleotide constructs and nuclear proteins are efficiently transferred into cells. The polynucleotide constructs is rapidly transported into the nuclei of cultured cells. Moreover, when the polynucleotide constructs and nuclear protein are co-introduced into non-dividing cells in rat liver by injection into rat portal veins, the polynucleotide constructs is carried into liver cell nuclei efficiently by nuclear protein for expression in the rat liver.

Alternatively, the polynucleotide constructs can be introduced into cells by the method of Remy et al., *Proc Natl Acad Sci USA* 92(5): 1744–8 (1995), a modular transfection system based on lipid-coated polynucleotide particles reminiscent of enveloped viruses. The particle core is composed of the lipopolyaminc-condensed polynucleotide in an electrically neutral ratio to which other synthetic lipids with key viral properties are hydrophobically adsorbed. Good transfection level can be achieved simply with the neutral core particle, provided a zwitterionic lipid (dioleoyl phosphatidylethanolamine) is added to completely coat the recombinant polynucleotide. Addition of lipids with a triantennary galactosyl residue drives the neutral nucleolipidic particles to the asialoglycoprotein receptor of liver cells: Transfection increases approximately 1000-fold with 25% galactolipid. These electrically silent particles provide an attractive solution for gene transfer in vivo where the external saccharide coat allows the particles to diffuse within the organism and reach target cells.

In another embodiment, the common stem/progenitor cells are derived from transgenic animals, and thus are in a sense already genetically modified. There are several methods presently used for generating transgenic animals. The technique used most often is direct microinjection of DNA into single-celled fertilized eggs. Other techniques include retroviral-mediated transfer, or gene transfer in embryonic stem cells. These techniques and others are detailed by Hogan et al. in *Manipulating the Mouse Embryo, A Laboratory Manual* (Cold Spring Harbor Laboratory Ed., 1986). Use of these transgenic animals has certain advantages including the fact that there is no need to transfect healthy neurospheres. Common stem/progenitors to liver cells and pancreatic cells derived from transgenic animals will exhibit stable gene expression. Using transgenic animals, new genetic combinations can be bred. The transgenic animal may have integrated into its genome any useful gene that is expressed by liver or pancreatic cells.

For long-term, high-yield production of polypeptide of interest, stable expression is preferred. Rather than using expression vectors which contain viral origins of replication, host cells can be transformed with the cDNA controlled by appropriate expression control elements (e.g., promoter, enhancer, sequences, transcription terminators, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media.

A number of selection systems may be used, including but not limited to the herpes simplex virus thymidine kinase, hypoxanthine-guanine phosphoribosyltransferase, and adenine phosphoribosyltransferase genes can be employed in tk$^-$, hgprt$^-$ or aprt$^-$ cells respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin genes. Additional selectable genes have been described, namely trpB, which allows cells to utilize indole in place of tryptophan; hisD, which allows cells to utilize histinol in place of histidine; and ODC (ornithine decarboxylase) which confers resistance to the ornithine decarboxylase inhibitor, 2-(difluoromethyl)-DL-ornithine, DFMO.

Increased expression can be achieved by increasing or amplifying the vector copy number using amplification methods well known in the art. Such amplification methods include, e.g., DHFR amplification (see, e.g., Kaufman et al., U.S. Pat. No. 4,470,461) or glutamine synthetase ("GS") amplification (see, e.g., U.S. Pat. No. 5,122,464). Expression vectors containing the geneticin (G418) or hygromycin drug selection genes are also useful. These vectors can express both a coding polynucleotide of interest and a gene conferring resistance to selection with toxin such as G418 or hygromycin B. The G418 resistance gene codes for aminoglycoside phosphotransferase (APH) which enzymatically inactivates G418 added to the culture medium. Only those cells expressing the APH gene will survive drug selection usually resulting in the expression of the second biologic gene as well. The hygromycin B phosphotransferase (HBH) gene codes for an enzyme that specifically modifies hygromycin toxin and inactivates it. Genes co-transfected with or contained on the same plasmid as the hygromycin B phosphotransferase gene will be preferentially expressed in the presence of hygromycin B.

In vitro culture of pancreatic ducts Techniques and methods culturing pancreatic islets are known to those of skill in the art. See, for example Freshney, supra and the references cited therein; Humanson (*Aninal Tissue Techniques,* 4th Edition, W. H. Freeman and Company, 1979); and Ricciardelli et al. (*In Vitro Cell Dev. Biol.* 25: 1016–1024, 1989). In one embodiment, the purification of ducts from transgenic and non-transgenic mice is accomplished using the procedures of Kerr Conte et al., *Diabetes* 45(8): 1108–14 (1996). Pancreatic tissue was extracted and placed in a collagen gel. Cysts structures form in vitro. In another embodiment, the culture of ducts is used to develop cultures of duct epithelial cells. Specific embodiments are provided in EXAMPLE 5 and 6.

Islets can be isolated from pancreas tissue by methods known to those skilled in the art. See, for example, Beattic & Hayek, International Patent Application WO 98/26044. The term "islets" is used herein to include both adult islets of Langerhans and islet-like cell clusters.

Pancreatic duct culture can be performed in liquid tissue culture medium, which includes any liquid solution that contains the appropriate solutes to preserve living cells and tissues. Many types of mammalian tissue culture media are available from commercial suppliers, such as Sigma Chemical Co., St Louis Mo.; Aldrich Chemical Co., Inc.; Milwaukee, Wis.; and Gibco BRL Life Technologies, Inc., Grand Island N.Y. Examples of commercially available culture media are Basal Medium Eagle, CRCM-30 Medium, CMRL Medium-1066, Dulbecco's Modified Eagle's Medium (DMEM), Fischer's Medium, Glasgow Minimal Essential Medium, Ham's F-10 Medium, Ham's F1-12 Medium, High Density medium, Iscove's Modified Dulbecco's medium, Leibovitz's L-15 Medium, McCoy's 5A Medium (modified), Medium 199, Minimum Essential Medium Eagle, Alpha Minimum Essential Medium, Earle's Minimum Essential Medium, Medium NCTC 109, Medium NCTC 135, RPMI-1640 Medium, William's Medium E, Waymouth's MB 752/1 Medium, and Waymouth's MB 705/1 Medium. Other media suitable for use in the methods of the invention are listed in Atlas et al. (*Handbook of Microbiological Media*, CRC Press, Baoca, Raton, Fla., 1993) and in Freshney (*Cutler on Animal Cells, A Manual of Basic Technique*, 3d Edition, Wiley-Liss, New York, 1994). Media that are suitable for use in the methods of the invention may be supplemented, when appropriate, with insulin. Insulin is commercially available from several sources, including Eli Lilly and Company (Indianapolis, Ind.) and Novo Nordisk Pharmaceuticals (Denmark).

Incubation is generally performed under conditions known to be optimal for cell growth. Such conditions can include for example a temperature of approximately 37° C. and a humidified atmosphere containing approximately 5% $CO_2$. The duration of the incubation can vary widely, depending on the desired results. In general, incubation is preferably continued until the cells begin to lose enough of their insulin secretion functionality to impose significant limits on their usefulness. As an approximate rule, the loss of over 25% of the rate of insulin secretion relative to fresh cells may be considered a limit. The degree of growth is conveniently expressed as an increase in the DNA content of the cell population, and a preferred degree of growth is an approximately three-fold or more increase in DNA content. Expressed as a range, a preferred degree of growth is an increase in DNA content from about three-fold to about twelve-fold.

Pancreatic duct culture can also be performed using the method of U.S. Pat. No. 5,681,587, issued Oct. 28, 1997, to Halberstadt et al. This method increases the number of adult pancreatic islet cells, by contacting the cells with laminin 5 extracellular matrix. When islet cells are contacted with the deposited matrix containing laminin 5, an increase in cell number is observed. The expanded islet cells contain insulin and respond to glucose challenge.

Identification of PDX-1$^+$ endocrine progenitor cells in the regenerating pancreas of the IFNγ transgenic mouse In another aspect, the invention provides a method for the use of the homeobox protein PDX-1 as a marker for pancreatic stem/progenitor cells, including a common stem/progenitor to liver cells and pancreatic cells. PDX-1 is clearly involved in pancreatic development and is expressed in the fetal pancreas during ontogeny. In EXAMPLE 7, histological analyses characterized the progenitor cell responsible for ductal proliferation and islet regeneration.

Significant PDX-1 expression also occurs in a subset of ductal epithelial cells in the regenerating transgenic pancreata, the cells having morphological and histological characteristics of ductal epithelial cells. PDX-1 expression was found in both lumenal and perilumenal ductal epithelial cells. Insulin expression, characteristic of the newly formed islet structure, is also present in a subpopulation of PDX-1 expressing ductal cells. The PDX-1 expressing ductal cells are found in both perilumenal and lumenal locations, and a subset of the PDX-1 expressing cells also express insulin. Thus, PDX-1 expression in the regenerating ducts of the INFγ transgenic mouse recapitulates the requirement for PDX-1 during ontogeny, and defines PDX-1 as an important pancreatic progenitor cell marker in the regenerating pancreas. The derivation of new endocrine cells from ducts exhibiting significant expression of PDX-1, coupled with PDX-1 expression in the regenerating duct epithelium, shows that new formation during INFγ mediated regeneration in the INFγ transgenic mouse might proceed through mechanisms similar to those active during fetal development.

The following examples are presented to more fully illustrate the preferred embodiments of the invention. These examples should in no way be construed as limiting the scope of the invention, as defined by the appended claims.

EXAMPLE 1

Expression of KGF in the Islets of Langerhans Leads to Pancreatic hepatocyte Generation and Duct Cell Proliferation To better understand the role of KGF in pancreatic development, a model system was established in which the influence of localized KGF expression on the growth and development of the pancreas can be assessed. A transgenic mouse model was constructed in which expression of the murine KGF-coding polynucleotide controlled by the human insulin promoter, resulting in KGF expression within beta cells in the islets of Langerhans. Ectopic KGF expression resulted in several changes to the pancreas, as described below. The ins-KGF mouse therefore provides a valuable system for studies designed to enhance understanding of pancreatic growth and development.

Generation of ins-KGF transgenic mice To generate ins-KGF transgenic mice, the 585 base pair (bp) KGF cDNA was obtained by reverse transcriptase polymerase chain reaction (RT-PCR) of mRNA from mouse salivary glands. The KGF cDNA was cloned into a vector containing the human insulin promoter and the Hepatitis b 3' untranslated polynucleotide. The ins-KGF fragment of the vector was isolated by low melt agarose, purified using Geneclean (BIG 101 Inc., La Jolla, Calif.) and NACS Prepac DNA purification columns (BRL, Gaithersburg, Md.), and microinjected into fertilized zygotes from BALB/c×C57BL/6 F2 mice. Transgene positive mice were further bred with BALB/c mice.

Expression of the transgene message in the islets of ins-KGF mice In situ hybridization of pancreatic sections taken from two lines of ins-KGF transgenic mice showed that expression of the transgene message was concentrated in islets of Langerhans. In situ hybridization was carried out as described by Amush et al., *Lab Invest* 74: 985–990 (1995). Antisense and sense riboprobes were prepared by in vitro transcription of a linearized plasmid containing KGF cDNA using [$^{35}$S]-UTP. After in situ hybridization, sections were covered with photographic emulsion and exposed for 4 weeks before developing.

Emergence of pancreatic hepatocytes in the islets of ins-KGF mice revealed by histological analysis and immunohistochemistry These two lines of ins-KGF transgenic mice were further characterized. Pancreata and spleens were fixed overnight in 10% neutral buffered formalin (3.6% formaldehyde) and embedded in paraffin. Spleen sections were stained in conjunction with pancreatic slices as controls for pancreas-specific antibodies. 5 μm paraffin sections were either stained with hematoxylin and eosin (H&E) for conventional histological evaluation or stained for the presence of insulin, glucagon, somatostatin, pancreatic polypeptide, amylase, CAII, PDX-1, albumin, alpha-fetoprotein, or bromodeoxyuridine (BrdU) using immunocytochemical techniques described by Gu & Sarvetnick, *Development* 118: 33–46 (1994). Briefly, sections were deparaffinized and blocked with 2% normal goat serum before applying the primary antibodies for insulin, glucagon, somatostatin (all from DAKO, Carpentaria, Calif.), PDX-1, pancreatic peptide or alpha-fetoprotein (both from ICN Immuno Biologicals, Costa Mesa, Calif.), albumin (Accurate Chemical and Scientific Corporation, Westbury, N.Y.), amylase (Sigma, St. Louis, Mo.), BrdU (Accurate/Sera-Lab, Westbury, N.Y.), or CAII (Biodesign, International, Kennebunk, Me.). Binding of the primary antibody was detected using the appropriate secondary antibody (Vector Laboratories, Burlingame), and the horseradish peroxidase (HRP)-labeled avidin-biotin complex (ABC kit, Vector Laboratories). HRP was visualized using 3,3'-diaminobenzidine as a substrate. Gill's hematoxylin was used as a counterstain for all sections.

Morphological changes to islet structure in ins-KGF typically appear in ins-KGF mice between 5–7 months of age and are minimal in young mice. Interestingly, clear changes were found in the cellular composition of the islets. Although some normal endocrine cells were present (beta, delta, and PP cells), many of the cells within many of the islets of the transgenic pancreas were not typical pancreatic cells. Extremely large cells with large nuclei were observed in the periphery of approximately one third to one half of the islets. To determine the relative sizes of islets in ins-KGF transgenic and negative littermate mice, anti-insulin stained sections were examined. Islets were measured at 10× power (Zeiss Axioscope), using the known 100 μm length of the crosshairs at 10× power for comparison. Islet size was assessed as either small (<100 μm diameter), medium (200–400 μm) or large (>400 μm). Sixteen ins-KGF and twelve negative littermate mice were evaluated and ten islets were counted for each mouse. The islet sizes of young (less than 3 months) and old (greater than 3 months) mice were compared.

Found in approximately ⅓ to ½ of the islets and localized in the periphery of the islets, these novel cells were often found to encompass more than ½ the area of the islet. These cells were large, with respect to both their overall size and the size of their nuclei, in contrast to the islets of non-transgenic control mice, in which the cells were of a uniform size. The large cells occurred on the periphery of islets, or in trails in close association with islets. The large cells were not observed in other regions of the transgenic pancreas. The large cells did not express insulin, glucagon, somatostatin, pancreatic polypeptide, amylase, CAII, or PDX-1 (a marker for the beta and delta cell lineages in the adult), nor did they express Meca-32, a marker for endothelial cells. These cells did not appear to be endocrine, exocrine, ductal, or endothelial, but were similar in morphology to hepatocytes and did express the liver protein, albumin.

Alpha-fetoprotein and albumin staining identified the large cells as pancreatic hepatocytes within islets of ins-KGF mice. Albumin is normally expressed by adult hepatocytes, while alpha-fetoprotein is expressed by hepatocytes during liver development and regeneration. While alpha-fetoprotein is not typically found within the normal adult pancreas, it was strongly upregulated in the large cells first identified by H&E. Alpha-fetoprotein expressing cells were not detected in non-transgenic littermate control mice. All of the larger cells were positive for alpha-fetoprotein expression, ⅔ of the larger cells were positive for albumin expression. The large cells which were positive for albumin were intensely stained and were clearly visible above the background. Thus, this EXAMPLE shows the presence of hepatocytes localized in the islets of KGF expressing transgenic mice.

Enhanced duct cell proliferation in KGF-expressing mice Additional morphological changes were also seen within the islets of the transgenic pancreas. In general, the islets became progressively larger as the mice aged, and a distended and folded epithelial cell mass was observed populating the islets. No such morphological changes were observed in non-transgenic littermate control mice. On average, significantly more large islets (>400 μm diameter) were found in ins-KGF mice three months of age and older than in non-transgenic littermates (p=0.017). While it is clear that the islets of transgenic mice express the prototypical pancreatic islet hormones produced by non-transgenic mice (insulin, glucagon, somatostatin, and pancreatic polypeptide), the hormone staining cells of transgenic mice were in small clusters surrounding this distended cell mass.

Importantly, the distended epithelia were identified as ductal cells by their expression of carbonic anhydrase II (CAII), which is highly expressed in pancreatic duct cells. CAII positive cells were found to compose the intra-islet ducts of ins-KGF mice, while PDX-1, a transcription factor known to be expressed within the islets of adult mice, is not found within the ductal cells of a consecutive section. While the islets stain positive for PDX-1, the distended epithelia do not. These epithelial cells were not found to express any of the endocrine hormones either, nor did they express amylase, normally expressed by acinar cells. The presence of these enlarged ductal regions within the islets suggested ongoing proliferation in the duct cell populations.

Indeed, hyperproliferative activity was clearly demonstrated in experiments using BrdU to monitor cell proliferation. For assessment of cellular proliferation, 100 mg/g body weight BrdU (Serva, Heidelberg, Germany) was injected intraperitoneally into mice 16 hours before sacrifice. Paraffin-embedded pancreata were sectioned and stained with an anti-BrdU antibody (Accurate Chemical Westbury, N.Y.) as described above after treatment with 2.8 N HCl for 15 minutes. BrdU positive cells were counted in transgenic and non-transgenic mice (n=6 for each genotype). The mitotic index was calculated by dividing the number of positively stained nuclei of cells comprising the duct wall with that of total nuclei/duct wall in at least five randomly chosen fields in each pancreas. Ductal cells were identified by morphology and CAII staining.

Increased proliferation within pancreata of ins-KGF transgenic mice was measured by the proliferating cells staining brown, indicating that they have incorporated BrdU. A mitotic index of 1.6% was measured for ins-KGF mice, while that of the non-transgenic littermates was 0.16%. This latter value is comparable to what has been previously reported by Githens (*Journal of Pediatric Gastroenterology and Nutrition* 7: 486–506, 1988). The difference in these mitotic indices is statistically significant (p<0.001). Additionally, although the majority of BrdU positive (proliferating) cells were ductal, an increased number of BrdU positive cells were within both the endocrine and exocrine tissues, in comparison to non-transgenic mice.

Thus, this EXAMPLE shows the expression of KGF in the islets of the pancreas results in substantial proliferation of duct cells within the islet mass. Despite the morphological differences in the pancreata of transgenic mice, no pathology, hyperglycemia, or hypoglycemia was found to be associated with KGF expression in the islets of transgenic mice. No morphological changes were observed in the liver, kidney, or intestine of the ins-KGF transgenic mice.

EXAMPLE 2

Transgenic Expression of EGF in Pancreatic Beta Cells Results in Substantial Morphological Changes EGF was ectopically expressed in transgenic mice using a human insulin promoter. The beta cell-targeted expression of EGF resulted in significant morphological changes, including cellular proliferation and disorganized islet of Langerhans growth. The mice were normoglycemic. Interestingly, insulin-producing beta cells were found in some of the ducts of older ins-EGF transgenic mice. This EXAMPLE therefore shows that both EGF can affect pancreatic development and growth.

Generation of ins-EGF transgenic mice To determine the influence of EGF expression in the beta cells of the pancreas, transgenic mice expressing murine EGF under control of the human insulin promoter were generated (ins-EGF). The 280-bp EGF cDNA was used to generate the ins-EGF transgenic mouse. The cDNA was cloned into a vector containing the human insulin promoter and the hepatitis b 3' untranslated polynucleotide. The ins-EGF fragment was isolated by low melt agarose, purified using Geneclean (BIO 101 Inc., La Jolla, Calif.) and NAGS Prepac DNA purification columns (BRL, Gaithersburg, Md.), and microinjected into fertilized zygotes from (Balb/c×C57BL16) $F_2$ mice. Progeny were screened for the presence of the transgene by PCR typing of tail DNA that was extracted using proteinase K digestion overnight. PCR was performed using two 24-mer primers specific for the human insulin promoter. Transgene-positive mice were further bred with BALB/c mice.

Transgenic mice were screened by PCR and were further bred with BALB/c mice for four generations from the original (Balb/c×C57BL/6) $F_2$ mice. The transgenic mice appeared normal and healthy, with average life spans.

Expression of the transgene message in the islets of ins-KGF mice Expression patterns of EGF were characterized by immunohistochemistry. Pancreata were fixed overnight in 10% neutral buffered formalin (3.6% formaldehyde) and embedded in paraffin. 5 µm paraffin sections were either conventionally stained with H&E for histological evaluation or stained for the presence of insulin, glucagon, somatostatin, amylase or BrdU using immunocytochemical techniques. Sections were deparaffinized and blocked with 2% normal goat serum before applying the primary antibodies for insulin, glucagon, amylase or somatostatin (all from DAKO, Carpentaria, Calif.), or BrdU (Accurate/Sera-Lab, Westbury, N.Y.). Binding of the primary antibody was detected using the appropriate secondary antibody (Vector Laboratories, Burlingame, Calif. or Boehringer-Mannheim, Indianapolis, Ind.), and the horseradish peroxidase (HRP)-labeled avidin-biotin complex (ABC kit, Vector Laboratories). HRP was visualized using 3,3'-diaminobenzidine as a substrate. Gill's hematoxylin was used as a counterstain.

The expression of EGF significantly upregulated in all transgenic islets. As expected, EGF was expressed at low levels in the islets of non-transgenic littermate controls. While the level of the EGF receptor (EGF-R) appeared comparable to the constitutive level of expression previously observed for this receptor by Damjanov et al., (*Lab Invest* 55: 582–592, 1986), upregulation of the EGF-R was detected in the ductal epithelia of the transgenic pancreas.

Morphological changes of ins-EGF mice Ins-EGF transgenic mice had dramatic morphological changes within their pancreata. While the pancreatic ducts appeared normal in the transgenic mice, the islets increased in size as the mice aged. After 3 months of age, the mice had significantly more islets of larger size (>400 µm) than did their non-transgenic littermates, in which most islets were <100 µm (p<0.008).

In addition, the transgenic islets exhibited substantial disaggregation. Disorganization of islet architecture increased with age in ins-EGF mice. Three month old and seventeen month old ins-EGF mice stained with H&E revealed little mononuclear cell infiltration to the irregularly shaped islets that increased in size and complexity with age. Age and sex matched non-transgenic control littermate stained with H&E demonstrated typical islet morphology and no immune infiltration.

Significant fibrosis occurred around the islets. Pancreatic lymphocytic infiltration was minor and was not sufficient to explain the disorganized architecture of the islets. Surprisingly, the lymphocyte infiltration at three months did not increase significantly with age. The observed lymphocytic infiltration and structural changes in the islets were not observed in non-transgenic littermates.

Immunostaining for insulin, glucagon, somatostatin, and amylase in the ins-EGF mouse revealed typical expression patterns within the islets and exocrine tissue, similar to age and sex-matched non-transgenic controls. Morphological changes occur at a later age than in ins-EGF×KGF mice, and are less severe than in double transgenic mice. Non-transgenic demonstrated delayed and lesser phenotype changes than in single transgenic. Additionally, the cells producing these proteins were, for the most part, present in typical numbers and placement. However, the rare presence of insulin-positive cells was detected in some ducts at 17 months, implying the generation of newly formed beta cells within the pancreatic ducts. Beta cells are not normally found outside of the islets. The overall health and viability of ins-EGF mice matched that of non-transgenic littermates.

Blood glucose values were taken at 2 week intervals for mice of various ages. Blood was obtained from the tail and blood glucose levels were determined using Glucofilm blood glucose test strips (Miles Diagnostic, Elkhart, Ind.). Non-fasting blood glucose values of non-transgenic Balb/c mice in our colony ranged from 80 to 160 mg/dl. No mouse exceeded the normoglycemic value of 150 mg/dl, nor was any mouse found to be hypoglycemic.

EXAMPLE 3

Transgenic Expression of EGF and KGF in Pancreatic Beta Cells Results in Substantial Morphological Changes Two important growth factors for pancreatic development, EGF and KGF, were ectopically expressed in transgenic mice using the human insulin promoter. The beta cell-targeted expression of either EGF or KGF resulted in significant morphological changes, including cellular proliferation and disorganized islet of Langerhans growth. In both cases, the mice were normoglycemic. Intercrossing the individual ins-EGF and ins-KGF transgenic mice to generate Ins EGF×KGF mice resulted in transgenic mice with more profound changes in pancreatic morphology than was seen for either growth factor alone. Proliferation of pancreatic cells was also observed in the double transgenic mouse, as was extensive intra-islet fibrosis, which was found to increase in severity with time. Interestingly, insulin-producing beta cells were found in some of the ducts of older ins-EGF and ins-EGF×KGF transgenic mice, and amylase-producing cells were observed within the islet structures of the double transgenic mice.

This EXAMPLE therefore shows that both EGF and KGF can affect pancreatic development and growth. Co-expression of these growth factors acted in concert to produce striking morphological changes in the pancreas, without causing any apparent abnormalities in pancreatic function.

Generation of ins-EGF×KGF transgenic mice To determine the effects beta cell-expression of EGF and KGF would have on pancreatic development and function, ins-EGF mice were crossed to ins-KGF mice, and ins-EGF×KGF progeny were interbred to homozygosity for both transgenes. Once both lines had been backcrossed to Balb/C mice for four generations, individual homozygote ins-EGF and ins-KGF mice were mated and progeny interbred to create homozygous, double transgenic (ins-EGF×KGF) mice.

Synergistic effects of combined EGF and KGF on pancreatic morphology Characterization of the double transgenic mice revealed unusual changes in pancreatic morphology which did not simply reflect the effects of each individual transgene. ins-EGF×KGF mice developed enlarged, distended, and non-confluent islets at earlier times than was seen for either the single ins-EGF or ins-KGF transgenic mice. Additionally, all of the transgenic mice, age 3 months or greater, had significantly more islets of larger size (>400 $\mu$m diameter) than did non-transgenic mice, in which most islets were <100 $\mu$m ($p<0.02$). In this regard, the double transgenic mice had more islets of larger size than did the ins-KGF transgenic mice ($p<0.02$), and there appeared to be more islets of a larger size in the double transgenic mice than in the ins-EGF mice, although the difference was not as significant ($p<0.07$). Morphological changes to the islets continued to develop as the mice aged. That is, islet networks and ductule development were much greater in the double transgenic mice than in either single transgenic mouse. Furthermore, there appeared to be an increase in the number of intra-islet ductules. Although islets were enlarged, distended, and lobulated to varying degrees for each transgenic mouse, individual beta cells remained intact and functional as demonstrated by insulin staining. Interestingly, as with the ins-EGF mouse, insulin positive cells were also observed in some of the ducts of the ins-EGF×KGF transgenic mice at a later age (6 months). In addition, normal blood glucose levels were measured over the animals life span (90–150 mg/dl).

Immunostaining for insulin, glucagon, somatostatin, and amylase in the ins-EGF mouse revealed typical expression patterns within the islets and exocrine tissue, similar to age and sex-matched non-transgenic controls. Morphological changes occur at an earlier age in ins-EGF×KGF mice, and are more severe than in single transgenic mice. Three month old and six month old ins-EGF×KGF mice stained with anti-insulin antibody and counterstained with blue hematoxylin showing increasingly larger, and more disorganized networks of islets. Non-transgenic demonstrated delayed and lesser phenotype changes in single transgenic mice and normal morphology in non-transgenic controls. Additionally, the cells producing these proteins were, for the most part, present in typical numbers and placement. However, the rare presence of insulin-positive cells was detected in some ducts at 17 months, implying the generation of newly formed beta cells within the pancreatic ducts; beta cells are not normally found outside of the islets. In spite of the lymphocyte infiltration and unusual islet morphology, the overall health and viability of ins-EGE mice matched that of non-transgenic littermates.

Synergistic effects of combined EGF and KGF on cell proliferation To assess the effects of EGF and KGF on cell proliferation, mice were injected with BrdU. BrdU incorporation into pancreatic cells was determined by immunohistochemistry. Cellular proliferation was quantified by injecting 100 mg/g body weight BrdU (Serva, Heidelberg, Germany) intraperitoneally into mice 15 hours prior to sacrifice. Paraffin-embedded pancreata were sectioned and stained with an anti-BrdU antibody (Accurate Chemical, Westbury, N.Y.) as described above after treatment with 2.8 N HCl for 15 minutes. The extent of proliferation was determined by counting all the BrdU positive cells within 20 fields using a 20× objective. These 20 fields were representative of all the BrdU positive cells per pancreatic slice, yet were also normalized for the area measured for each mouse. At least 5 mice of each genotype were counted, for quantification of the average number of BrdU positive cells per pancreatic slice.

On average, ins-EGF and ins-KGF mice had 6.8+1–2 (n=5) and 11.0+1–3.8 (n=6) BrdU positive cells, respectively. By contrast, the double transgenic mice had 15.3+/3.1 (n=8) and the non-transgenic littermates had 0.7+1/–0.3 (n=6) positive cells. All three lines of transgenic mice had significantly more pancreatic cell proliferation than did the control mice ($p<0.01$). While the majority of the proliferating cells of the ins-KGF mouse were identified as ductal in EXAMPLE 1, morphological examination indicated that proliferating cells of the ins-EGF and of the ins-EGF×KGF mice were found within the acinar, islet, and ductal tissues.

As with the ins-EGF mice, pancreatic lymphocytic infiltration was minor and did not increase with age in the double transgenic ins-EGF×KGF mouse. Intra-islet fibrosis was found in ins-EGF×KGF islets, but not immune infiltration. H&E staining revealed a low level of immune infiltration to ins-EGF×KGF transgenic mice even with advanced age. Interestingly, much more extensive intra-islet fibrosis was observed in the double transgenic mice than was observed in the ins-EGF mice. The fibrosis is characterized by spindle shaped cells with elongated nuclei. The level of fibrosis increased substantially with age in the double transgenic mice.

Synergistic effects of combined EGF and KGF on induction of exocrine cells Unexpectedly, exocrine cells, which stain positive for amylase, are present within the islets of double transgenic mice. Such positive staining was not observed within the islets of either single transgenic mouse or non-transgenic control. Anti-amylase antibody stained with brown chromogen against a blue hematoxylin counterstain revealed atypical endocrine as well as the expected exocrine staining within the pancreata of ins-EGF×KGF mice. In progressive stages in the evolution of this phenomenon, amylase-positive cells are first engulfed by adjacent islets. Acinar cells staining positive for amylase were surrounded by islet tissue and fibrotic cells. Later, amylase positive cells without distinct acinar cell morphology were also found within islet tissue. Importantly, the morphological changes that occur within the pancreata of the ins-EGF×KGF double transgenic mice do not appear to hinder normal functioning of the pancreas.

EXAMPLE 4

KGF Induces Differentiation of Endocrine Cells from Ductal Epithelial Cells

A transgenic mouse strain in which IFNy is expressed in pancreatic beta cells exhibits a continual development of new endocrine cells that arise throughout adult life (Gu & Sarvetnick, *Development* 118: 33–46 (1994)). The ontogeny of beta cells appears to be quite similar to fetal development. To show that IFNγ induces the expression of growth factors that facilitate this regenerative process, ins-IFNy transgenic mice were constructed. The ins-IFNγ transgenic mice have regenerated islets that bud into the duct lumen from duct epithelial cells, cells which express elevated levels of KGF adjacent to the duct wall. Cells expressing the KGF receptor (KGFR) are also found within the duct wall of the transgenic mice. Neutralizing α-KGF antibody treatment of these mice modulates the regeneration process, resulting in beta cell insufficiency and hyperglycemia. Also, fetal pancreata exposed to the neutralizing α-KGF antibody exhibit abnormal islet development. Therefore, KGF mediates the islet regeneration observed in ins-IFNγ/NOD transgenic mice, is involved in pancreatic development, and enhances the maintenance and expansion of a ductally-derived cell that is capable of differentiating into functional precursor cells for the endocrine pancreas.

Introduction The pancreas develops from both an epithelial component of endodermal origin and a mesenchymal component of mesodermal origin. The merging of these two components results in a classic epithelial-mesenchymal interaction. Several studies have implicated a soluble "mesodennal factor" that is required for maintenance of the pancreatic epithelium. Studies of pancreatic ontogeny, carcinoma of the pancreas, and models of limited pancreatic regeneration point to the ductal epithelium as the site where exocrine and endocrine development originates.

The role of growth factors in pancreatic islet development is difficult to address experimentally, because beta cells arise during midgestation, allowing the determination of relevant growth factors during embryonic stages. The beta cell numbers are stable after birth. Nevertheless, pancreatic islet cell regeneration is important for studying regulatory factors involved in pancreatic islet cell differentiation.

Transgenic mouse expressing IFNγ under the control of insulin To identify growth factors that regulate pancreatic islet development, the expression of growth factors were assessed in a model where islet cell regeneration occurs continuously. In the model, elevated KGF RNA levels are found, as well as KGF receptor expression by a population of ductal epithelial cells.

Transgenic mice expressing IFNγ have been described previously by Sarvetnick et al. *Cell* 52:773–782 (1988). Progeny from this line were backcrossed more than twelve generations to NOD/Shi mice. Progeny were screened for the presence of the transgene by PCR typing of tail DNA, extracted using proteinase K digestion overnight. PCR was performed using two 24-mer primers specific for the human insulin promoter.

In situ hybridization To screen for potential growth factors that could mediate the observed proliferation and differentiation in the transgenic mice, the ins-IFNγ transgenic mouse pancreata was screened for increased expression of nine potentially relevant growth-inducing factors by in situ hybridization. In situ hybridization was carried out as described by Arnush et al., *Lab Invest* 74: 985–990 (1995). Antisense and sense riboprobes were prepared by in vitro transcription of a linearized plasmid containing KGF cDNA using $^{35}$S-UTP. After in situ hybridization, sections were covered with photographic emulsion and exposed for 4 weeks before developing.

These in situ hybridization assays of pancreatic sections from ins-IFNγ transgenic mice revealed expression of KGF RNA near actively replicating ducts, as judged by their size, and in the vicinity of regenerated islets, as judged by their proximity to ducts. This demonstrates that the cells adjacent to the duct wall, likely fibroblasts, produce KGF.

The ability to detect KGF implied that cells near the duct may respond to a signal from this growth factor. Pancreatic cells that respond to the KGF mitogenic signal were predicted to express the KGF receptor. Using an antibody probe consisting of the KGF molecule fused to the $IgG_1$ Fc portion of the immunoglobulin molecule (α-KGFR), to identify the pancreatic cells that could respond to KGF by screening for KGFR expression.

Binding of the α-KGFR molecule was revealed in a subcategory of cells in the duct wall of ins-IFNγ/NOD transgenic mouse pancreata. These cells were found mainly in the periluminal location, and occasionally bordering the duct lumen. The KGFR localized in the cytoplasm, indicating potential transport of the receptor to the cell surface or internalization of the receptor after activation by binding to KGF. The receptor-positive ductal cells expressing KGFR were also spherically shaped, compared with the cuboidal appearance of other ductal cells, and the perilumenal location indicates migration away from the lumen of the duct, which occurs during beta cell ontogeny in this model. No KGFR positive cells were found in the duct wall of non transgenic littermate pancreatic tissue. This EXAMPLE demonstrated that cells capable of responding to KGF activity within the differentiating epithelia, but were not detectable in epithelia of the normal adult pancreas.

Neutralizing α-KGF antibody To determine that KGF was required for islet neogenesis in this model, the transgenic mice were treated with a neutralizing α-KGF antibody. Neutralizing α-KGF antibody treatment of ins-IFNγ/NOD transgenic mice reduced cell replication associated with pancreatic islet cell regeneration and lead to the development of diabetes. Fetal pancreata treated with the neutralizing α-KGF antibody were apparently defective in normal development of ducts and seeding of islets.

Ins-IFNγ/NOD transgenic mice were derived by backcrossing IFNγ transgenic mice with NOD mouse strain seven times. These mice were treated with either neutralizing antibody or control antibody for a short (two week) period, to transiently deplete the growth factor from the transgenic mice. The mice were monitored for replication of pancreatic cells and diabetes during and following the antibody treatment.

Ins-IFNγ/NOD transgenic mice were treated with a neutralizing 1G4 α-KGF monoclonal antibody (Bottaro et al., 1993; Alarid et al., 1994). Antibody treatment was performed as follows: Ascites fluid containing neutralizing anti-KGF antibodies was purchased from Lofstrand Laboratories (Bethesda, Md.). The antibody was purified over a protein G column (Pharmacia Biotech, Alameda, Calif.) and analyzed for KGF neutralizing activity. Animals were injected with 30 μg/g body weight of neutralizing anti-KGF antibody, IgG, sterile PBS or nothing two times a week for two weeks before sacrifice (4 mice were sacrificed one week later with no additional treatment).

Interestingly, neutralizing α-KGF antibody treatment resulted in a rapid increase in blood glucose levels. Blood glucose measurement was performed as follows: At regular intervals, blood was obtained from the tail and blood glucose levels were determined using Glucofilm blood glucose test strips (Miles Diagnostic, Elkhart, Ind.).The increase in blood glucose levels implies a reduction in insulin producing beta cells mass in the anti-KGF treated animals, and is consistent with the theory that KGF is involved in the regeneration process.

BrdU labeling To determine that the removal of KGF correlated with a reduction in proliferative activity in progenitor cells within the duct wall were labeled the anti-KGF treated transgenic NOD mice with BrdU. For assessment of cellular proliferation, 100 μg/g body weight BrdU (Serva, Heidelberg, Germany) was injected intraperitoneally into mice 12 hours before sacrifice. Paraffinembedded pancreata were sectioned and stained with an anti-BrdU antibody (Accurate Chemical, Westbury, N.Y.) as described above after treatment with 2.8 N HCl for 15 minutes. The mitotic index was calculated by dividing the number of positively stained nuclei of cells comprising the duct wall with that of total nuclei/duct wall in at least five randomly chosen fields in each pancreas. Immunohistochemical techniques were used to visualize the BrdU labeled replicating cells, which were counted. BrdU incorporation was lower in ducts of mice treated with a-KGF (9%) than in controls treated with IgG (14%)(P<0.05). This reduction indicates the arrest of division of a subcategory of ductular intermediate cells. Thus, KGF plays a role in pancreatic islet regeneration in the transgenic model.

Fetal studies To determine whether KGF is necessary for fetal islet differentiation, BALB/c mice were treated at day 10 of gestation with the neutralizing α-KGF antibody, an IgG isotype that readily crosses the placenta. BALB/cByJ mice were allowed to mate and Day 0 of pregnancy was indicated by the presence of a vaginal plug. Pregnant mice were injected with 1.5 μg of neutralizing α-KGF antibody on day 9 and fetuses were taken on day 17, embedded whole in paraffin, sectioned and analyzed by immunocytochemistry as described above.

Fetal pancreata deprived of KGF at the E10 stage show a decrease in the number of insulin-producing cells and abnormal clustering of insulin producing cells, indicating a defect in the formation of islets. The islets in control IgG-treated mice appeared to be dispersed away from the main duct, whereas in neutralizing α-KGF antibody-treated mice, the islets were bordered by duct-like cells. the studies suggest a requirement for KGF during normal fetal islet development.

Summary This EXAMPLE shows the trophic activities of KGF in the neogenesis of beta-cells, at least during pancreatic islet regeneration in the transgenic models. In situ hybridization with a KGF probe showed upregulation of the KGF message in ins-IFNγ transgenic mice. KGFR expression is found in a subset of ductal epithelial cells as well, identifying a target cell for KGF action. KGF was required for islet cell regeneration in the transgenic mouse model since its depletion leads to a decrease in duct cell replication and hyperglycemia in the transgenic mice. Furthermore, studies of transgenic mice expressing this factor demonstrated expansion of the epithelium and small duct associated islets.

Several critical differences exist between the prior art and the results of this EXAMPLE.

The availability of common stem/progenitor cells to be stimulated by KGF is one important issue. The availability of common stem/progenitor cells in the transgenic mice here is much greater than the normal adult animals in the KGF infusion studies. In the transgenic mice, intermediate cells exist in adult animals that could be uniquely sensitive to the KGF signal. Thus, the trophic effects of this growth factor may only be revealed in situations where an appropriate population of common stem/progenitor cells was present. In the generation of islet cells, duct epithelium proliferation is followed by differentiation forming a hierarchical relationship. Therefore, in the regeneration model, islet cell development was affected through the duct epithelium, which precludes islet cells during the process of neogenesis.

EXAMPLE 5

In Vitro Cultures of pancreatic Ducts

Isolation and culture of mouse pancreatic ducts The purification of duct epithelia from transgenic and non-transgenic juice was accomplished using the procedures of Kerr Conte et al., *Diabetes* 45(8): 1108–14 (1996). Pancreatic tissue was extracted and placed in a collagen gel. Cysts structures formed in vitro.

Approximately 10 cysts have been obtained from each transgenic or non-transgenic mouse, without optimizing the isolation conditions. Better yields of duct cysts per pancreas (approximately 40 cysts from each transgenic or non-transgenic mouse) can be obtained after optimization of isolation procedures.

Purified ducts have been incubated in vitro for up to ten days. Histological analysis has verified the identity and integrity of the ducts. For this histological analysis, the ducts were removed from the dish in the gel, fixed in 10% neutral buffered formalin, and embedded in paraffin. After being sectioned and placed on glass slides for microscopic analysis, the ducts were stained by hematoxylin and eosin (H&E) staining to distinguish individual cells. The sectioned ducts were also analyzed for expression of insulin, carbonic anhydrase, and glucagon by immunostaining. These isolation procedure resulted in the purification of ducts of a wide variety of sizes in diameter.

Cultured ducts have been labeled with BrdU to determine the proportion of duct cells that proliferate in tissue culture.

Engraftment of purified ducts Techniques have been developed to transplant isolated, purified, viable pancreatic ducts into syngeneic recipients, to provide purified common stem/progenitor populations.

To develop a proof of principle, whole in vitro grown duct cysts have been transplanted into mice. Purified pancreatic ducts have been successfully engrafted into the liver. A 3 mM wide and three mM deep incision was made into the lower lobe of the liver. One duct cyst was placed into the incision. The pancreatic duct has been retained in the graft site for at least one week following this grafting procedure.

Purified pancreatic ducts can be engrafted into the liver and other sites for further stem cell studies.

EXAMPLE 6

Stem Cell Assay

The invention provides an assay for the presence and activity of common stem/progenitor to liver cells and pancreatic cells.

To demonstrate stem cells in the hematopoietic system, purified mouse bone marrow hematopoietic stem cells (HSC) were used to reconstitute all blood cell types in lethally irradiated mice (Spangrude et al., *Science* 241(4861) :58–62 (1988)). Subsequently, significant advances led to elegant experiments in which a single $mCD34^{10/-}$ c-kit$^+$, Sca-1$^+$ Lin- cell resulted in long term reconstitution of all blood cell types by Osawa et al., (1996). Furthermore, studies have shown that a single Lin, IL-7R$^+$ Thy-1, Sca-1$^+$ c-kit$^+$ cell can generate both T and B cells, identifying this cell type as the earliest known lymphoid-committed progenitor in mouse bone marrow (Kondo et al., *Cell* 91(5) :661–72 (1997)).

Single cell clonal analyses have also been used to characterize stem cell activity in vitro. Studies have demonstrated that a single mammalian neural crest cell is multipotent and is capable of giving rise to neurons and Schwann cells in culture (Stemple & Anderson, *Cell.* 71(6): 973–85. (1992)). In addition, single cell analyses of the embryonic CNS have shown that purified stem cells are capable of producing all three major cell types of the CNS (neurons, astrocytes, and oligodendrocytes) in culture (Davis & Temple, 1994; Reynolds & Weiss, 1996; Kalyani et al., 1997). Stem cells have also been demonstrated in the testes of donor mice; isolated cells are able to repopulate the sterile testes of recipient mice, leading to the production of spermatozoa (Brinster & Avarbock, *Proc Natl Acad Sci USA* 91(24):11303–7 (1994); Brinster & Zimmerman, *Proc Natl Acad Sci USA* 91(24): 11298–302 (1994)).

Based on differential adhesion to extracellular matrix components, human epidermal stem cells have also been isolated and characterized by Jones, *Clin Sci (Colch)*.91(2) :141–6 (1996). In this case, stem cells isolated from cultured epidermis are clonogenic, are able to self-renew, and are able to generate differentiated keratinocytes in vitro. Cultured epidermal stem cells are able to reconstitute a complete epidermis when grafted onto nude mice.

To critically evaluate the activity of common stem/progenitor to liver cells and pancreatic cells, cells are tested for the ability to reconstitute pancreatic islets or hepatocytes. The stem cell assay places purified duct cells in ectopic sites in syngeneic recipients in vivo to detect the seeding of new pancreatic islets or hepatocytes from the implanted pancreatic common stem/progenitor cells.

Stem cell assays are performed using transgenic or non-transgenic fetal pancreas. The grafts are either from ins-KGF transgenic mice or non-transgenic BALB/c donors, transplanted into BALB/c SCID recipients. Next, purified whole pancreatic ducts are used in the stem cell assay. Subsequently, duct fragments are used in the stem cell assay. Finally, purified dispersed fractionated duct cells are used in the stem cell assay, to isolate common stem/progenitors to liver cells and pancreatic cells.

The newly seeded islets are identified from their location in the graft site in vivo. The newly seeded islets are also identified using sensitive labeling techniques. KGF transgenic mouse were crossed with the ROSA 26 line to produce double transgenic offspring that express the β-galactosidase gene in all of their cells. These double transgenic pancreatic ducts are used as donors in stem cell assays, to demonstrate the presence of common stem/progenitors to liver cells and pancreatic cells in the ducts of ins-KGE transgenic mice.

Transgenic and non-transgenic fetal pancreata have been transplanted under the kidney capsule, resulting in the growth of mature islets within three weeks of implantation.

EXAMPLE 7

Identification of PDX-1$^+$ Endocrine progenitor Cells in the Regenerating pancreas of the IFNγ Transgenic Mouse The present EXAMPLE was initiated in order to further define and characterize the endocrine progenitor cells in the ducts of INFγ transgenic mice that give rise to islet cells, and to identify novel cell markers associated with these cells.

The identification of novel markers associated with endocrine progenitor cells in the INFγ transgenic pancreas would clearly be of value, with regards to both defining these precursor cells and in an analysis of the regenerative process. Thus, this EXAMPLE sought to identify proteins whose expression might be elevated in the regenerating ducts of the INFγ transgenic mouse. The initial analysis focused on the homeobox-containing protein, PDX-1.

PDX-1 was selected because this protein had been implicated in pancreatic development during ontogeny. PDX-1 (also called IDX-1, IPF-1, or STF-1) is a transcription factor critical for pancreatic development and endocrine cell formation. PDX-1 regulates the expression of insulin. PDX-1 is expressed in the pancreatic islets of adults, but is absent from duct cells. Mice that do not express PDX-1 lack a pancreas and die shortly after birth. PDX-1 functions in the determination and maintenance of the pancreatic identify of common precursor cells, or in the regulation of their propagation. Because of the extensive duct cell proliferation and new islet growth characteristics of the INFγ mouse, PDX-1 was suspected of being involved in the regeneration occurring in the INFγ mouse. A protein which is critical for endocrine cell development during ontogeny might also be critical for this process during new islet formation in the regenerating pancreas.

Transgenic mouse model A transgenic mouse model in which INFγ expression results in the destruction of existing islets has previously been described by Sarvetnick et al. *Cell* 52:773–782 (1988). Ins-IFNγ transgenic mice, which express IFNγ in the beta cells of the pancreatic islets, display ductal hyperplasia and destruction of islets by infiltrating lymphocytes, characteristic of that seen in Type I diabetes mouse models. An intriguing phenotype of these mice is the balance between regeneration of "new" islets and the destruction of pre-existing islets in the acinar tissue. The newly formed islets bud into the lumen of the ducts, where they are protected from infiltration and destruction. The aggressive growth of pancreatic ducts and the continuous differentiation of new endocrine cells during adult life indicates that the progenitor cells responsible for this remarkable regrowth exist in the transgenic pancreas.

Ins-INFγ mice that were backcrossed into the NOD/Shi strain (ins-INFγ/NOD) for more than ten generations have a very low incidence of diabetes (<20%, compared to NOD mice, which have an incidence of ~80% for females and ~25% for males). Significant pancreatic duct cell proliferation and islet regeneration are observed in these mice. The absence of significant regenerative abilities by endocrine cells shows that the new islet growth is mediated by progenitor cells in the pancreata of transgenic mice, because the new islet cells are derived from cells in the pancreatic duct.

Immunoelectron Microscopy Using immunoelectron microscopy (IEM), the PDX-1 expressing cells present in mice were characterized. Pancreatic tissue was fixed in 10% normal buffered formalin (3.6% formaldehyde) for 2 hours at 25° C. Fixed tissue was infused in 1.5 M sucrose-PBS for 0.5 hours with gentle inversion periodically. Infused tissue was quick frozen in liquid nitrogen, embedded in O.C.T. and 2-methybutane and sectioned 30–40 $\mu$m thick. These sections were incubated in glycine-PBS to quench aldehyde for 0.5 hours, blocked in 10% normal goat serum for 0.5 hours, incubated for 1 hour each in PDX-1 (primary antibody) and a goat anti-rabbit secondary antibody before refixing in 1% glutaraldehyde-PBS for 0.25 hours and washing in PBS. Reaction product was visualized with diaminobenzidine (DAB) for 7 minutes and DAB$^+$ H$_2$O$_2$ for 4 minutes before treating with 1% OsO$_4$. Tissue was dehydrated in graded ethanol, cleared in propylene oxide and embedded in liquid Spurr resin. Thin sections were viewed with a Hitachi HU 12A electron microscope.

Immunohistochemistry The PDX-1 expressing cells present in mice were also characterized by immunhistochemistry. Pancreata were fixed overnight in 10% neutral buffered formalin (3.6% formaldehyde) and embedded in paraffin. 5 $\mu$m paraffin sections were either conventionally stained with hematoxylin and eosin (H&E) for histological evaluation or stained for the presence of insulin, PDX-1, using immunocytochemical techniques. Briefly, sections were deparaffinized and blocked with 2% normal goat serum before applying the primary antibodies for insulin (DAKO, Carpentaria, Calif.), or PDX-1. Binding of the primary antibody was detected using the appropriate secondary antibody (Vector Laboratories, Burlingame, Calif.), and the horseradish peroxidase (HRP)-labeled avidin-biotin complex (ABC kit, Vector Laboratories). HRP was visualized using 3,3'-diaminobenzidine as a substrate. Gill's hematoxylin was used as a counterstain.

Results Significant PDX-1 expression was observed in a subset of ductal epithelial cells in the regenerating pancreas of the INFγ mouse by light and immunoelectron microscopy. PDX-1 expression was found in both lumenal and perilumenal ductal epithelial cells. No morphological differences were apparent between PDX-1 positive and PDX-1 negative duct cells. Insulin expression, characteristic of the newly formed islet structure, was also detected in a subpopulation of PDX-1 expressing ductal cells.

PDX-1 expression in the IFN-γ transgenic pancreas Previous studies have shown that INFγ transgenic mouse islets express the normal endocrine hormones (Gu & Sarvetnick, *Development* 118: 33–46 (1994)). In addition, consistent with what is observed in nontransgenic pancreata, the ductal epithelial cells in the IFNγ mouse pancreata express the ductal cell marker carbonic anhydrase II (CAII), with no apparent staining for amylase, a marker for acinar cells (Gu & Sarvetnick, *Development* 118: 33–46 (1994)). PDX-1 is clearly involved in pancreatic development and is expressed in the fetal pancreas during ontogeny.

To determine if PDX-1 is involved in regeneration as well as ontogeny, the INFγ regenerating pancreas of transgenic and nontransgenic mice was screened for PDX-1 expression with a polyclonal antibody against PDX-1. Striking expression of PDX-1 was found in the regenerating ducts of the INFγ mouse. The analyses revealed the presence of immunoreactivity in the nucleus of islet cells, as expected, but also in a large proportion of the cells within the duct wall. While not all of the cells within the pancreatic ducts of the transgenic mice were positive for PDX-1, those ducts supporting the growth of intraductal islets were strongly positive for PDX-1 expression. Staining of adjacent sections with antibody to insulin revealed that these PDX-1 positive ducts also contained a subpopulation of cells that were positive for insulin. As expected, the ducts from nontransgenic control mice did not express PDX-1 or insulin.

PDX-1 expression has not previously been observed in pancreatic duct cells.

Ultrastructural analysis of PDX-1 expressing duct cells Cells in the IFNγ regenerating ducts exhibit many of the morphological characteristics of ductal epithelial cells. These characteristics included centrally located, irregularly shaped nuclei, numerous interdigitating processes on the lateral aspects of the cells, unspecialized cytoplasm containing mitochondria, sparse elements of rough endoplasmic reticulum, scattered stacks of *Golgi lamellae,* and a variety of vesicular profiles. In addition, the apical plasma membrane possessed typical apical ultrastructural specializations including microvilli and junctional complexes complete with tight junctions.

Antibodies to PDX-1 in immunoelectron microscopy studies clearly revealed the presence of PDX-1 nuclear staining in a subset of ductal cells bordering the lumen, as well as in a subset of perilumenal ductal cells. No differences were observed in morphology between those ductal cells which expressed PDX-1 and those which did not.

Discussion Ins-INFγ transgenic mice pancreata display massive infiltration concomitant with the destruction of islets, disruption of the surrounding exocrine tissue, and proliferation of ducts. This destruction is balanced by the regeneration of islets that bud into the ductal lumen, where they are protected from destruction by infiltrating lymphocytes. In this EXAMPLE, histological analyses characterized the progenitor cell responsible for the remarkable ductal proliferation and islet regeneration.

The ductal epithelium, which consists of intercalated (small), intralobular (medium) and interlobular (large) ducts, has long been implicated as the site of exocrine and endocrine development in the pancreas. Studies of pancreatic ontogeny, carcinoma of the pancreas and models of limited pancreatic regeneration point to the ductal epithelium as the source of growth, differentiation and proliferation (Githens, 1988; Argent et al., 1992; McClean & Weaver, 1993; Pictet et al., 1972). The pancreatic ducts of the regenerating pancreas contain several types of transitional cells including endocrine cells expressing multiple hormones, endocrine/exocrine cells, duct/exocrine cells and exocrine cells (Gu & Sarvetnick, *Development* 118: 33–46 (1994)).

The endocrine cells may migrate away from the duct lumen, and that the cells bordering on the lumen might be the best candidates for "protodifferentiated" stem cells. In promoting regeneration and new islet formation, these progenitor cells recapitulate the early development of the pancreas. Parallels between ontogeny and IFNγ mediated regeneration exist. In both cases, endocrine gene expression is an early event, with individual endocrine cells initially appearing in the duct wall. These cells subsequently migrate to form clusters, which grow into fully differentiated islets. Thus, endocrine cell precursors could be abundant in the ducts of mice undergoing islet regeneration, as they are in the fetal pancreata.

Summary Using light and immunoelectron microscopy, PDX-1 expressing pancreatic cells were found in the transgenic pancreata that have morphological and histological characteristics of ductal epithelial cells. The PDX-1 expressing ductal cells are found in both perilumenal and lumenal locations, and a subset of the PDX-1 expressing cells also express insulin. Thus, PDX-1 expression in the regenerating ducts of the INFγ transgenic mouse recapitulates the requirement for PDX-1 during ontogeny, and defines PDX-1 as an important pancreatic progenitor cell marker in the regenerating pancreas. The derivation of new endocrine cells from ducts exhibiting significant expression of PDX-1, coupled with PDX-1 expression in the regenerating duct epithelium, shows that new formation during INFγ mediated regeneration in the INFγ transgenic mouse might proceed through mechanisms similar to those active during fetal development.

A number of embodiments of the present invention have been described. Nevertheless, various modifications may be made without departing from the spirit and scope of the invention. Accordingly, other embodiments are within the scope of the following claims.

We claim:

1. A transgenic mouse having incorporated into its genome a polynucleotide sequence comprising a human insulin promoter operably linked to a keratinocyte growth factor (KGF)-coding polynucleotide sequence, wherein said KGF-coding polynucleotide sequence is expressed in the pancreatic cells such that said mouse exhibits in its pancreas at least one of the following morphological changes selected from the group consisting of hyperproliferation of duct cells and disorganized growth of islet of Langerhans.

2. A transgenic mouse having incorporated into its genome a polynucleotide sequence comprising a human insulin promoter operably linked to an epidermal growth factor (EGF)-coding polynucleotide sequence, wherein said EGF-coding polynucleotide sequence is expressed in the pancreatic cells such that said mouse exhibits in its pancreas at least one of the following morphological changes selected from the group consisting of hyperproliferation of duct cells, disorganized growth of islet of Langerhans, and an increased number of intra-islet ductules.

3. The transgenic mouse of claim 1 further comprising incorporated into its genome a polynucleotide comprising a human insulin promoter operably linked to an EGF-coding polynucleotide, wherein said EGF-coding polynucleotide sequence and said KGF-coding polynucleotide sequence are expressed in the pancreatic cells such that said mouse exhibits in its pancreas at least one of the following morphological changes selected from the group consisting of hyperproliferation of duct cells, disorganized growth of islet of Langerhans, an increased number of intra-islet ductules, and extensive intra-islet fibrosis.

* * * * *

UNITED STATES PATENT AND TRADEMARK OFFICE
CERTIFICATE OF CORRECTION

| | |
|---|---|
| PATENT NO. | : 6,242,666 B1 |
| DATED | : June 5, 2001 |
| INVENTOR(S) | : Nora Sarvetnick, et al. |

It is certified that error appears in the above-identified patent and that said Letters Patent is hereby corrected as shown below:

Column 1,
Line 5, please insert:
-- GRANT SUPPORT
This invention was made with the United States Government Support under Contract No. HD29764 by the National Institutes of Health. The United States Government has certain rights in the invention. --

Signed and Sealed this

Thirtieth Day of October, 2001

*Attest:*

*Attesting Officer*

NICHOLAS P. GODICI
*Acting Director of the United States Patent and Trademark Office*